United States Patent [19]

Bronner et al.

[11] Patent Number: 4,849,117

[45] Date of Patent: Jul. 18, 1989

[54] CONCENTRATED COMPOSITION FOR FORMING AN AQUEOUS FOAM

[75] Inventors: James A. Bronner, Glendale; Ronald K. Ostroff, Shadow Hills, both of Calif.

[73] Assignee: Sanitek Products, Inc., Los Angeles, Calif.

[21] Appl. No.: 64,171

[22] Filed: Jun. 17, 1987

[51] Int. Cl.[4] .................... C09K 21/00; A62D 1/08; B01J 13/00; A61K 9/00

[52] U.S. Cl. .................... 252/3; 169/46; 252/6.5; 252/8.05; 252/307; 252/350; 252/382; 252/603; 252/607; 252/611

[58] Field of Search .................... 252/2, 3, 4, 6, 6.5, 252/8.05, 182.1, 382, 307, 350-352; 169/45, 46, 66, 68; 424/43, 44; 134/40

[56] References Cited

U.S. PATENT DOCUMENTS

| | | | |
|---|---|---|---|
| Re. 29,649 | 5/1978 | Farnsworth | 252/8 |
| 3,394,768 | 7/1968 | Chocola et al. | 252/3 |
| 3,422,011 | 1/1969 | Jackovitz et al. | 252/3 |
| 3,457,172 | 7/1969 | Stewart et al. | 252/3 |
| 3,480,546 | 11/1969 | Bashaw et al. | 252/3 |
| 3,579,446 | 5/1971 | Kroke et al. | 252/3 |
| 3,933,674 | 1/1976 | Fransworth | 252/171 |
| 3,956,138 | 5/1976 | Crockett | 252/3 |
| 3,957,658 | 5/1976 | Chiesa, Jr. et al. | 252/3 |
| 3,984,334 | 10/1976 | Hopper | 252/8.05 |
| 4,049,556 | 9/1977 | Tujimoto et al. | 252/3 |
| 4,058,493 | 11/1977 | Prokai et al. | 252/351 |
| 4,149,599 | 4/1979 | Chiesa, Jr. | 169/47 |
| 4,278,552 | 7/1981 | Hisamoto et al. | 252/3 |
| 4,303,534 | 12/1981 | Hisamoto et al. | 252/3 |
| 4,331,555 | 5/1982 | Baskent et al. | 252/351 |
| 4,350,206 | 9/1982 | Hoffmann et al. | 169/47 |
| 4,384,988 | 5/1983 | Schoenholz et al. | 252/610 |
| 4,424,133 | 1/1984 | Mulligan | 252/8.05 |
| 4,439,329 | 3/1984 | Kleiner et al. | 252/8.05 |
| 4,442,018 | 4/1984 | Rand | 252/3 |
| 4,511,488 | 4/1985 | Matta | 252/162 |
| 4,594,167 | 6/1986 | Kobayashi et al. | 252/3 |

FOREIGN PATENT DOCUMENTS

| | | | |
|---|---|---|---|
| 49-23713 | 6/1974 | Japan | 252/3 |

*Primary Examiner*—Howard J. Locker
*Attorney, Agent, or Firm*—Spensley Horn Jubas & Lubitz

[57] ABSTRACT

A concentrate composition for forming a stable aqueous foam. The concentrate composition comprises an anionic surfactant, a solvent and a stabilizer. The surfactant is preferably the sodium salt of an alpha olefin sulfonate such as sodium dodecyl sulfonate. The solvent is preferably a $C_2$–$C_8$ diol, and the stabilizer is a $C_{10}$–$C_{18}$ alcohol.

35 Claims, No Drawings

CONCENTRATED COMPOSITION FOR FORMING AN AQUEOUS FOAM

BACKGROUND OF THE INVENTION

1. Field of the Invention

The present invention relates to a concentrate composition for forming an aqueous foam. Specifically, the present invention concerns a concentrate composition suitable for use in forming stable, economical aqueous foams which foams are suitable for use as fire suppressant foams particularly fire suppressant foams for use in fighting wildland fires.

In the past, it has been known to use aqueous foams for a variety of purposes. Such foams have been used in security systems, as foam drilling fluids for deep well drilling and as fire fighting agents. Other uses for aqueous foams are apparent to those skilled in the art.

In a relatively recent innovation, aqueous foams have proven extremely effective in combating forest fires. Typically, such aqueous foams are formed by discharging a water/foaming agent mixture from a water scooping aircraft flying above the site of the forest fire. The water/foaming agent mixture "flash foams" upon discharge from the plane and falls onto the forest fire. For ground use applications the water/foaming agent mixture is foamed by passing it through an air aspirating nozzle or by employing an air injection delivery system known as a WEP's system to those skilled in the art. The foams function in much the same way as water, that is, they serve to "wet" the fuel. Unlike water, the aqueous foams coat the fuel (trees, etc.) thus keeping the water where it will best penetrate into the fuel. As can be understood by the described process, converting water into an aqueous foam allows a greater fire suppressant activity to be achieved from a given amount of water than if said water were applied directly to the fire. This is achieved through the increased surface area of the water due to the foaming process.

Foams possessing slower drain rates are generally better wildland fire suppressants since they hold the water up in the fuel for longer periods of time. The drainage rate of foams is directly related to the expansion ratio of the foams. An increase in the expansion ratio results in a slower drainage rate. However, the higher the expansion ratio the less water is actually present in a given volume of foam. Finally, drainage rate is inversely proportional to the square of the size of the foam bubbles. As can be appreciated from the above, the effectiveness of a particular foam is dependent on a variety of factors including bubble size, expansion ratio, water content, and drainage rate.

A major problem in combating forest fires is transporting water to the site of the fire. The use of an aqueous foam which provides a greater amount of fire suppressant activity to be developed from a given amount of water is, therefore, highly desirable.

Additionally, the use of aqueous foams in combating forest fires has the advantage that such foams impact relatively gently upon the vegetation to which they are applied as compared to the impact water causes when dropped from a source such as an airplane. Additionally, the use of aqueous foams allows the water present therein to cling to vegetation and resist run off into the soil, thereby increasing the fire suppressant activity of the water present therein.

Aqueous foams suitable for use in combating fires are known in the art. Exemplary of such foams are the foams described in U.S. Pat. No. 3,186,943 issued June 1, 1965 to Barthauer. Barthauer claims a method of generating a fire extinguishing foam from a concentrate which concentrate consists essentially of the ammonium alkyl ether sulfate of about 4 moles of ethylene oxide with 1 mole of $C_{10}$ to $C_{20}$ aliphatic fatty alcohol and an aliphatic fatty alcohol selected from the class consisting of lauryl alcohol and myristyl alcohol in an amount of up to 12 and one-half percent by weight of said sulfate.

U.S. Pat. No 4,442,018 issued Apr. 10, 1984 to Rand, describes a stabilized aqueous foam system and concentrate and method for making them. Rand discloses a foam concentrate comprising a combination of a water soluble polymer of the polyacrylic acid type, a foam stabilizer of dodecyl alcohol, a surfactant, a solvent and water.

As indicated by the two cited U.S. Patents, the use of concentrates in forming aqueous foams for use in fire fighting applications are known. Nonetheless, prior art concentrates and foams formed therefrom have demonstrated certain undesirable qualities. For example, the foam concentrates described by Barthauer and Rand are unsatisfactory in that they contain flammable solvents which lower the flash points of the concentrates themselves thus making them more difficult to use safely. Additionally, the concentrates are not concentrated enough to render them suitable for use in wildland fire fighting since they need to be added to water in amounts which are too high to allow economical use.

The concentrates described by Rand have proven undesirable in that they are added to water at levels of 6–10 percent. These levels also render said concentrates unacceptable for use in fighting wildland fires. Moreover, the concentrates of Rand are somewhat difficult to mix into water, a characteristic which also makes them unsuitable for use in fighting wildland fires.

SUMMARY OF THE INVENTION

It is an object of the present invention to produce a concentrate composition for forming stable aqueous foams which concentrate is capable of being used at very low levels thus rendering it suitable for use in fighting wildland fires. Additionally, it is an object of the present invention to provide a concentrate composition which is easily mixed with water thus requiring little, if any, agitation.

Accordingly, the present invention concerns a concentrate composition for forming an aqueous foam which foam is highly stable and therefore possessed of a relatively slow drain rate. Additionally, the concentrate composition of the present invention has a viscosity which renders it suitable for use in conventional foam forming equipment.

Applicants have found that a concentrate composition possessing the described characteristics is formed from about 10 to about 70 weight percent of an anionic surfactant; from about 2 to about 50 weight percent of a stabilizer selected from the group consisting of $C_{10}$–$C_{18}$ alcohols, and from about 2 to about 50 weight percent of a solvent capable of solublizing the stabilizer, and all weight percents being based on total concentrate composition weight.

DETAILED DESCRIPTION OF THE INVENTION

The concentrate compositions of the present invention comprise from about 10 to about 70 weight percent, beneficially from about 20 to about 50 weight percent, and preferably from about 30 to about 40 weight percent, based on total concentrate composition weight of an anionic surfactant. Surfactants suitable for use in the present invention should be capable of forming stable films in the foams formed from the concentrate composition thereby imparting a high degree of stability to the foams formed from the concentrate compositions.

Anionic surfactants which are capable of forming a highly stable film in foams formed from the concentrate compositions of the present invention are suitable for use in said concentrate compositions. Selection of suitable anionic surfactants can be aided by reference to *McCutcheon's Detergents and Emulsifiers*, North American Edition, 1981.

Beneficially, the anionic surfactant is selected from the group consisting of the salts of alpha olefin sulfonates having from 10 to 18 carbon atoms per molecule and mixtures thereof. Most beneficially, the surfactant is selected from the group consisting of the sodium, potassium or ammonium salts of alpha olefin sulfonates having from 10 to 18 carbon atoms per molecule and mixtures thereof. Preferably, the surfactant is selected from a group consisting of sodium dodecyl sulfonate, sodium tridecyl sulfonate, sodium tetradecyl sulfonate, sodium pentadecyl sulfonate, sodium hexadecyl sulfonate, sodium octadecyl sulfonate and mixtures thereof. The most preferred surfactant is a mixture of the sodium salts of the alpha olefin sulfonates having 12–16 carbon atoms per molecule.

The mixture of sodium salts of alpha olefin sulfonates has been found to be the preferred surfactant for use in the present invention due to its ability to form a stable foam regardless of the type of water employed. That is, applicants have discovered that by using a surfactant comprising the described mixture, the concentrates formed therefrom produce stable foams even when said foams are formed from sea water.

In the past, forming aqueous foams from sea water has proven difficult. This is because of the high concentration of dissolved minerals present in said sea water. Typically, the various ions present in sea water have interfered with the ability of the surfactant to form a stable foam.

The concentrate compositions of the present invention generally comprise a major portion of surfactant. When the surfactant employed is a sodium salt of an alpha olefin sulfonate, the surfactant is generally present in the compositions of the present invention in an amount of from about 30 to about 50 weight percent. It is to be understood that reference to the weight percent of surfactant present in the concentrate compositions refers to the weight percent of the active surfactant. The stability of the foam and the degree of foaming depends to a large extent on the surfactant employed and the amount of surfactant employed.

Applicants have discovered that when the surfactant is a sodium salt at an alpha olefin sulfonate (NaAOS) having from 10 to 18 carbon atoms per molecule that those surfactants with relatively few carbon atoms per molecule (10–12) produce a concentrate composition with good flash foaming capabilities. Those surfactants (NaAOS) with a relatively high number of carbon atoms per molecule (16–18) produce a concentrate composition with good stability.

In one preferred embodiment of the present invention, the surfactant employed is a mixture of sodium salts of various alpha olefin sulfonates. Specifically, the surfactant comprises sodium olefin sulfonates having 14 to 16 carbon atoms per molecule in combination with sodium dodecyl sulfonate. The $C_{14}$–$C_{16}$ NaAOS is present in an amount of from about 50–75, preferably from about 65–70 weight percent based on total surfactant weight. The sodium dodecyl sulfonate is present in an amount of from about 25–50, preferably, from about 30–35 weight percent based on total surfactant weight.

The sodium salts of the alpha olefin sulfonates suitable for use in the present invention are generally supplied as aqueous solutions containing less than 45%, by weight, of the sodium salt of the alpha olefin sulfonate. While it is possible to produce a more concentrated powder form of the sodium salt of the alpha olefin sulfonate, it is generally not economically feasible to exclusively employ such concentrated powders. In general, applicants have found it desirable to employ a combination of an aqueous solution of one or more sodium alpha olefin sulfonate (less than 45 weight percent sodium alpha olefin sulfonate, based on total weight) and an amount of a dried powder form of sodium alpha olefin sulfonate. In this manner Applicants are able to produce a concentrate composition comprising the desired concentration of surfactant. In one preferred embodiment Applicants employ a $C_{14}$–$C_{16}$ sodium alpha olefin sulfonate solution (40% NaAOS), a $C_{12}$ sodium alpha olefin solution (40% NaAOS), and a powdered form of a $C_{14}$–$C_{16}$ sodium alpha olefin sulfonate (greater than 90% NaAOS).

The concentrate compositions of the present invention comprise from about 2 to about 50 weight percent, beneficially from about 2 to about 10 weight percent and preferably from about 4 to about 10 weight percent, based on total concentrate composition weight, of a stabilizer selected from the group consisting of aliphatic alcohols having from about 10 to 18carbon atoms per molecule. The stabilizer is present in the concentrate compositions of the present invention in order to increase the foam viscosity of said concentrate compositions in dilute solutions thereby increasing the stability of the foam and slowing the drain rate. As a general rule, the slower the drain rate the better the foam is for use as a fire suppressant. Exemplary of the stabilizers suitable for use in the present invention are the aliphatic alcohols having from 10 to 18 carbon atoms per molecule. Exemplary of such alcohols are dodecanol (lauryl alcohol), tetradecanol (myristyl alcohol), hexadecanol (palmityl alcohol), and octadecanol (stearyl alcohol), and mixtures thereof. The preferred stabilizer is a mixture of $C_{12}$–$C_{16}$ aliphatic alcohols. This mixture of $C_{12}$–$C_{16}$ alcohols is preferred because it produces a concentrate composition having good flash foaming properties and good stability.

Applicants have discovered that it is desirable that the stabilizer be present in the concentrate compositions of the present invention in an amount of from about 15 to about 30 weight percent based on total weight of the surfactant. For example, if the concentrate composition comprises 35 weight percent of a surfactant, it is desirable that the concentrate composition comprise from about 5.25 to about 10.5 weight percent stabilizer based on total concentrate composition weight.

The stabilizer selected affects both the drain rate of foams produced from the concentrate compositions and the "pour points" of the concentrates themselves. "Pour-point" is defined as the temperature at which it is no longer possible to efficiently pour the concentrate compositions from a storage container. As the number of carbon atoms per molecule increases, the drain rate decreases. That is, the water drains from the foam more slowly. Correspondingly, as the number of carbon atoms per molecule increases, the pour point of the concentrate compositions increases.

The concentrate compositions of the present invention further comprise from about 2 to about 50 weight percent, beneficially from about 10 to about 40 weight percent, and preferably from about 20 to about 30 weight percent, based on total concentrate composition weight, of a solvent. The solvent present in the concentrate compositions of the present invention must be capable of solubilizng the stabilizer in the concentrate compositions of the present invention. The stabilizers of the present invention ($C_{10}$–$C_{18}$ alcohols) are generally known as fatty alcohols and tend to be relatively insoluble in aqueous solutions. The solvents of the present invention solubilize the stabilizers of the concentrate compositions. Any composition capable of solubilizing the stabilizer in the concentrate compositions of the present invention is suitable for use as the solvent of the present invention.

It is generally desirable that the concentrate compositions of the present invention be relatively non-flammable. That is, it is desirable that the solvent or solvents employed therein be selected such that the resultant concentrate compositions have a flashpoint of at least 170° F.

Exemplary of the solvents suitable for use in the present invention are the $C_2$–$C_8$ diols, the higher glycol ethers, mixtures of the above with d-limonene, and the like. Beneficial solvents are propylene glycol, butylene glycol, hexylene glycol, and mixtures thereof. The preferred solubilizer is hexylene glycol.

Hexylene glycol is preferred for use in the present invention due to its relatively low degree of toxicity compared to other $C_2$–$C_8$ aliphatic diols. Moreover, hexylene glycol has a relatively low density compared to, for instance, propylene glycol. Thus, a concentrate employing hexylene glycol weighs less per unit volume than a concentrate composition substituting, for instance, propylene glycol, for the hexylene glycol.

It has been found that certain co-solvent systems may be advantageous for use in the concentrate compositions of the present invention. For example, when hexylene glycol is used as the solvent, the resultant concentrate composition has a "pour point" of about 40° F. By using a co-solvent system it is possible to lower the "pour point" without deleteriously affecting the other properties of the concentrate compositions.

For example, by using d-limonene as a co-solvent with hexylene glycol it is possible to lower the pour point of the concentrate by almost 10° F. This is achieved by adding from about 1 to about 10 weight percent preferably from about 1 to about 5 weight percent most preferably from about 2 to about 4 weight percent, based on total concentrate composition weight of d-limonene to the concentrate compositions. The co-solvent of hexylene glycol and d-limonene comprises about 5–20 weight percent d-limonene and about 80–95 weight percent hexylene glycol based on total co-solvent weight. The preferred co-solvent comprises about 10 weight percent d-limonene and about 90 weight percent hexylene glycol based on total co-solvent weight.

In one preferred embodiment of the present invention, the concentrate composition comprises from about 30 to about 50 weight percent, based on total concentrate composition weight, of a sodium alpha olefin sulfonate having from 12 to 16 carbon atoms per molecule; from about 20 to about 30 weight percent based on total concentrate composition weight of hexylene glycol; from about 4 to about 8 weight percent, based on total concentrate composition weight, of a mixture of $C_{12}$–$C_{16}$ alcohols and the balance water. Applicants have found the above described embodiment of the present invention to be particularly advantageous in that the concentrate compositions possess a good balance of flash foaming capability and foam stability.

It is desirable that the concentrate composition of the present invention have a relatively neutral pH. That is, a pH of from about 6.5 to about 8.0. A composition having a relatively neutral pH is desirable because a neutral composition is less likely to damage the foliage to which it is applied and/or corrode the equipment in which it is used. Generally, compositions prepared as described above will have a basic pH (greater than about 7.0). Therefore, in order to produce a concentrate composition having a relatively neutral pH, it is necessary to add an acidic compound to the concentrate compositions of the present invention. Any acidic compound capable of producing a final concentrate composition having a relatively neutral pH which acidic compound can be added to the concentrated compositions of the present invention without undesirably effecting the physical properties or performance thereof is suitable for use in the present invention. Exemplary of acidic compounds suitable for use in the present invention are aqueous solutions of phosphoric acid, hydrochloric acid, acetic acid and the like. In the preferred embodiment of the present invention described above, the acidic component employed is a aqueous solution of phosphoric acid (75% phosphoric acid). The acidic component is added in trace amounts (less than about 0.5 weight percent).

The concentrate compositions of the present invention are prepared by any method of mixing which forms a generally homogenous mixture. Suitable methods of mixing will be apparent to those skilled in the art.

Methods of using the concentrate compositions of the present invention are known to those skilled in the art. Prior to foaming, the concentrate compositions are mixed with water, generally, the concentrate compositions of the present invention are mixed with water in an amount of from about 0.05 to about 10 parts concentrate composition per 100 parts water, beneficially from about 0.1 to about 2 parts concentrate composition per 100 parts water preferably from about 0.2 to about 0.8 parts concentrate composition per 100 parts water (based on volume). The amount of concentrate composition used in forming the water/concentrate composition mixture depends on the method of foaming to be employed, the type of water used, the amount of foam desired, and the like. The resulting water/concentrate composition mixture is then foamed.

Methods of foaming the water/concentrate composition mixtures are known to those skilled in the art. For fire suppressant applications, suitable foaming methods include flash foaming (dropping the mixture from an airplane) and passing the mixture through an air aspirating nozzle. The degree of expansion experienced by the concentrated composition/water mixture of the present invention is dependent on both the amount of concentrate employed in forming the mixture as well as the method of foaming the foam. Generally, for fire supressant applications, is desired that the concentrate composition/water mixtures according to the present invention have a relatively low expansion ratio on the order of 8–50 to 1, preferably about 10–15 to 1, meaning that the concentrate composition/water mixture will, after it is foamed, produce a foam material having 8–50 times preferably 10–15 times the volume of the concentrate composition/water mixture. It is to be understood that for other applications much higher expansion ratios may be desired. Expansion ratios on th order of 2,000 to 1 are possible.

In the following examples all weight percents are based on total concentrate composition weight.

EXAMPLE 1

A concentrate composition is formed by dispersing 12 weight percent of a dry powder of $C_{14}$–$C_{16}$ sodium olefin sulfonate (90% active, 10% inert) in 26 weight percent hexylene glycol. A uniform dispersion is formed with moderate agitation. In a separate vessel there is provided 27.5 weight percent of an aqueous solution of $C_{14}$–$C_{16}$ sodium olefin sulfonate (61% water 39% sodium olefin sulfonate); 27.5 weight percent of an aqueous solution of C12 sodium olefin sulfonate (61% water, 39% sodium olefin sulfonate); 5 weight percent of a $C_{12}$–$C_{14}$ aliphatic alcohol mixture and 2 weight percent deionized water. The contents of the vessel are mixed under moderate agitation. The hexylene glycol dispersion is then added, under agitation, to the contents of the vessel.

Six gallons of the resultant concentrate concentration is added to 1,000 gallons of water and allowed to disperse. The concentrate composition/water mixture is found to produce a stable foam having a flash foaming expansion ratio of about 13 to 1.

EXAMPLE 2

In a vessel there is mixed under moderate agitation: 4 weight percent of a $C_{12}$–$C_{14}$ aliphatic alcohol mixture; 50 weight percent of an aqueous solution of $C_{14}$–$C_{16}$ sodium olefin sulfonate (40% sodium olefin sulfonate, 60% water); 24 weight percent of an aqueous solution of a $C_{12}$ sodium olefin sulfonate (40% sodium olefin sulfonate, 60% water); 20 weight percent hexylene glycol and 2.0 weight percent d-limonene. The resultant concentrate composition is found to have a pour point of about 30°–35° F. and, when mixed with water at a concentration of about 0.6 percent and foamed, produces a desirably stable foam.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the following claims.

What is claimed is:

1. A concentrated composition for forming an aqueous foam, the composition comprising:

(1) from about 10 to about 70 weight percent, based on total concentrate composition weight, of an anionic surfactant selected from the group consisting of salts of alpha olefin sulfonates having from about 10 to about 18 carbon atoms per molecule and mixtures thereof;

(2) from about 2 to about 50 weight percent, based on total concentrate composition weight, of a stabilizer selected from the group consisting of $C_{10}$–$C_{18}$ alcohols;

(3) from about 2 to about 50 weight percent, based on total concentrate composition weight, of a solvent capable of solubilizing the stabilizer selected form the group consisting of $C_2$–$C_8$ diols, mixtures thereof and mixtures of one or more thereof with d-limonene; and (4) water.

2. The concentrate composition of claim 1 wherein the anionic surfactant is selected from the group consisting of the sodium salts, the potassium salts and the ammonium salts of alpha olefin sulfonates having from about 10 to about 18 carbon atoms per molecule and mixtures thereof.

3. The concentrate composition of claim 1 wherein the anionic surfactant is selected from the group consisting of the sodium salts of alpha olefin sulfonates having from about 10 to about 18 carbon atoms per molecule and mixtures thereof.

4. The concentrate composition of claim 1 wherein the anionic surfactant is present in an amount of from about 20 to about 50 wight percent, based on total concentrate composition weight.

5. The concentrate composition of claim 1 wherein the anionic surfactant is present in an amount of from about 30 to about 40 weight percent, based on total concentrate composition weight.

6. The concentrate composition of claim 5 wherein the anionic surfactant is a sodium salt.

7. The concentrate composition of claim 1 wherein the stabilizer is present in an amount of from about 2 to about 10 weight percent, based on total concentrate composition weight.

8. The concentrate composition of claim 1 wherein the stabilizer is present in an amount of from about 4 to about 10 weight percent, based on total weight concentrate composition.

9. The concentrate composition of claim 1 wherein the stabilizer is a mixture of alcohols having from about 12 to about 14 carbon atoms per molecule.

10. The concentrate composition of claim 8 wherein the stabilizer is a mixture of alcohols having from about 12 to about 14 carbon atoms per molecule.

11. The concentrate composition of claim 1 wherein the solvent is present in an amount of from about 10 to about 40 weight percent, based on total weight of the concentrate composition.

12. The concentrate composition of claim 1 wherein the solvent is present in an amount of from about 20 to about 30 weight percent, based on total concentrate composition weight.

13. The concentrate composition of claim 1 wherein the solvent is selected from the group consisting of the diols having from 1 to 8 carbon atoms per molecule.

14. The concentrate composition of claim 12 wherein the solvent is hexylene glycol.

15. The concentrate composition of claim 1 wherein the stabilizer is present in an amount of from about 15 to about 30 weight percent, based on total surfactant weight.

16. The concentrate composition of claim 6 wherein the stabilizer is present in an amount of from about 15 to about 30 weight percent, based on total surfactant weight.

17. The concentrate composition of claim 1 wherein the anionic surfactant and the stabilizer both have the same number of carbon atoms per molecule.

18. The concentrate composition of claim 1 wherein the concentrate composition comprises from about 1 to about 10 weight percent, based on total concentrate composition weight, of d-limonene.

19. The concentrate composition of claim 18 wherein the composition comprises from about 2 to about 4 weight percent, based on total concentrate composition weight, of d-limonene.

20. A concentrate composition for forming an aqueous foam, the composition comprising:
(1) from about 30 to about 40 weight percent, based on total concentrate composition weight, of an anionic surfactant selected from the group consisting of the sodium salts of alpha olefin sulfonates having from about 10 to about 18 carbon atoms per molecule;
(2) from about 4 to about 10 weight percent, based on total concentrate composition weight, of a stabilizer selected from the group consisting of $C_{10}$–$C_{18}$ alcohols;
(3) from about 20 to about 30 weight percent, based on total concentrate composition weight, of a solvent selected from the group consisting of $C_2$–$C_8$ diols, mixtures thereof and mixtures of one or more thereof with d-limonene; and
(4) water.

21. The concentrate composition of claim 20 wherein the surfactant is selected from the group consisting of the sodium salts of alpha olefin sulfonates having from 12 to 16 carbon atoms per molecule.

22. The concentrate composition of claim 20 wherein the stabilizer is selected from the group consisting of alcohols having from 12 to 14 carbon atoms per molecule.

23. The concentrate composition of claim 21 wherein the stabilizer is selected from the group consisting of alcohols having from 12 to 14 carbon atoms per molecule.

24. The concentrate composition according to claim 20 wherein the solvent is hexylene glycol.

25. The concentrate composition according to claim 23 wherein the solvent is hexylene glycol.

26. The concentrate composition of claim 23 wherein the stabilizer is present in an amount of from about 15 to about 30 weight percent, based on total weight of the surfactant.

27. The concentrate composition of claim 20 wherein the concentrate composition comprises from about 1 to about 10 weight percent, based on total concentrate composition weight, of d-limonene.

28. The concentrate composition of claim 27 wherein the concentrate composition comprises from about 2 to about 4 weight percent, based on total concentrate composition weight, of d-limonene.

29. A concentrate composition for forming an aqueous foam, the composition comprising:
(1) from about 30 to about 35 weight percent, based on total concentrate composition weight, of at least one sodium salt of an alpha olefin sulfonate having from 12 to 16 carbon atoms per molecule;
(2) from about 4 to about 8 weight percent, based on total concentrate composition weight, of a stabilizer selected from the group consisting of alcohols having from about 12 to about 14 carbon atoms per molecule;
(3) from about 20 to about 30 weight percent, based on total concentrate composition weight, of hexylene glycol; and
(4) water.

30. A concentrate composition for forming an aqueous foam, the composition comprising:
(1) from about 20 to about 50 weight percent, based on total concentrate composition weight, of at least one sodium salt of an alpha olefin sulfonate having from 12 to 16 carbon atoms per molecule;
(2) from about 2 to about 10 weight percent, based on total concentrate composition weight, of a stabilizer selected from the group consisting of $C_{10}$–$C_{18}$ alcohols;
(3) from about 10 to about 40 weight percent, based on total concentrate composition weight, of a co-solvent comprising 5–20 weight percent d-limonene, based on total co-solvent weight and from about 80–95 weight percent, based on total co-solvent weight, of a $C_2$–$C_8$ diol; and
(4) water.

31. The concentrate composition of claim 30 wherein the $C_2$–C8 diol is hexylene glycol.

32. A composition comprising;
(A) from about 0.2 to about 0.8 percent of a concentrate composition comprising:
(1) from about 10 to about 70 weight percent, based on total concentrate composition weight, of an anionic surfactant selected from the group consisting of salts of alpha olefin sulfonates having from about 10 to about 18 carbon atoms per molecule and mixtures thereof;
(2) from about 2 to about 50 weight percent, based on total concentrate composition weight, of a stabilizer selected from the group consisting of $C_{10}$–$C_{18}$ alcohols;
(3) from about 2 to about 50 weight percent, based on total concentrate composition weight, of a solvent capable of solubilizing the stabilizer selected from the group consisting of $C_2$–$C_8$ diols, mixtures thereof and mixtures of one or more thereof with d-limonene; and
(4) water; and
(B) from about 99.2 to about 99.8 percent water.

33. A composition comprising:
(A) from about 0.2 to about 0.8 percent of a concentrate composition comprising:
(1) from about 10 to about 70 weight percent, based on total concentrate composition weight, of an anionic surfactant selected from the group consisting of salts of alpha olefin sulfonates having from about 10 to about 18 carbon atoms per molecule and mixtures thereof;
(2) from about 2 to about 50 weight percent, based on total concentrate composition weight, of a stabilizer selected from the group consisting of $C_{10}$–$C_{18}$ alcohols;
(3) from about 2 to about 50 weight percent, based on total concentrate composition weight, of a solvent capable of solubilizing the stabilizer selected from the group consisting of hexylene glycol and mixtures thereof with d-limonene; and
(4) water; and
(B) from about 99.2 to about 99.8 percent water.

34. The composition according to claim 32 wherein the composition is foamed and has an expansion ratio of from about 8–50 to 1.

35. The composition according to claim 33 wherein the composition is foamed and has an expansion ratio of from about 8–50 to 1.

* * * * *